(12) United States Patent
Sotomayor

(10) Patent No.: US 7,935,355 B2
(45) Date of Patent: *May 3, 2011

(54) COMPOSITION AND METHOD FOR CONTROLLING INTESTINAL PATHOGENIC ORGANISMS

(75) Inventor: Konky Sotomayor, Palm Harbor, FL (US)

(73) Assignee: Nutritional Health Institute Laboratories, LLC, Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/025,568

(22) Filed: Feb. 4, 2008

(65) Prior Publication Data

US 2008/0260783 A1  Oct. 23, 2008

Related U.S. Application Data

(63) Continuation-in-part of application No. 11/737,483, filed on Apr. 19, 2007, now abandoned.

(51) Int. Cl.
 - *A61K 39/112* (2006.01)
 - *A61K 39/00* (2006.01)
 - *A61K 39/385* (2006.01)
 - *A61K 38/00* (2006.01)

(52) U.S. Cl. ............ 424/258.1; 424/184.1; 424/185.1; 424/192.1; 424/193.1; 424/194.1; 530/300

(58) Field of Classification Search .................. None
See application file for complete search history.

(56) References Cited

U.S. PATENT DOCUMENTS

| | | | |
|---|---|---|---|
| 3,674,863 A | 7/1972 | Fisher et al. | |
| 3,975,517 A | 8/1976 | Wilson | |
| 4,965,068 A | 10/1990 | Stephan et al. | |
| 4,971,794 A | 11/1990 | Linggood et al. | |
| 5,128,127 A | 7/1992 | Beck | |
| 5,132,288 A | 7/1992 | Johnson et al. | |
| 5,215,746 A | 6/1993 | Stolle et al. | |
| 5,538,727 A | 7/1996 | Stolle et al. | |
| 5,580,557 A | 12/1996 | Kramer | |
| 5,753,268 A | 5/1998 | Stolle et al. | |
| 5,792,452 A | 8/1998 | Linde | |
| 5,849,349 A | 12/1998 | Stolle et al. | |
| 5,853,765 A | 12/1998 | Stolle et al. | |
| 5,906,826 A | 5/1999 | Emery et al. | |
| 5,932,250 A | 8/1999 | Stolle et al. | |
| 6,027,736 A | 2/2000 | Emery et al. | |
| 6,056,978 A | 5/2000 | Beck et al. | |
| 6,231,871 B1 * | 5/2001 | Coloe | 424/258.1 |
| 6,399,074 B1 * | 6/2002 | Roland | 424/200.1 |
| 6,491,910 B1 * | 12/2002 | Schneitz et al. | 424/93.3 |
| 6,605,285 B2 | 8/2003 | Sharma et al. | |
| 6,706,267 B1 | 3/2004 | Adalsteinsson et al. | |
| 6,803,035 B2 | 10/2004 | Greenblatt et al. | |
| 6,866,847 B1 | 3/2005 | Kelly-Aehle | |
| 6,916,478 B2 | 7/2005 | Kadurugamuwa et al. | |
| 6,923,957 B2 | 8/2005 | Lowery et al. | |
| 2001/0009668 A1 | 7/2001 | Richardson | |
| 2001/0021386 A1 | 9/2001 | Nuijten et al. | |
| 2002/0012666 A1 | 1/2002 | Greenblatt et al. | |
| 2002/0028215 A1 | 3/2002 | Kadurugamuwa et al. | |
| 2002/0034530 A1 | 3/2002 | Emery et al. | |
| 2003/0064073 A1 | 4/2003 | Emery et al. | |
| 2004/0170639 A1 | 9/2004 | Kelly-Aehle | |
| 2004/0234550 A1 | 11/2004 | Fan et al. | |
| 2006/0024323 A1 | 2/2006 | Emery et al. | |
| 2006/0196428 A1 | 9/2006 | Correa et al. | |
| 2007/0148146 A1 | 6/2007 | Doyle et al. | |
| 2008/0220022 A1 * | 9/2008 | Le Gros et al. | 424/258.1 |

FOREIGN PATENT DOCUMENTS

| | | |
|---|---|---|
| AU | 75374/94 B | 3/1995 |
| EP | 0 006 695 B | 1/1980 |
| WO | 97/29768 | 8/1997 |
| WO | 03041734 | 5/2003 |
| WO | 2007/106956 | 9/2007 |

OTHER PUBLICATIONS

Van Immerseel et al (Avian Pathology, 2004, Abstract only).*
Ngeleka et al (Infection and Immunity, vol. 64, No. 8, p. 3118-3126).*
P.A. Chacana et al., "Protection Conferred by a Live *Salmonella* Eneteritids Vaccine Against Fowl Typhoid in Laying Hens," Avian Diseases, Jun. 2006, pp. 280-283, vol. 50, No. 2, American Association of Avian Pathologists. U.S.

* cited by examiner

*Primary Examiner* — Vanessa L. Ford
(74) *Attorney, Agent, or Firm* — Amin Talati, LLC

(57) ABSTRACT

An antigen composition for stimulating an immune response in an inoculated avian species to at least one intestinal pathogenic organism includes naturally-occurring wild *Salmonella enterica* subspecies in O-serogroups B, $C_3$ and D. Subspecies in O-serogroup B can include *Salmonella typhimurium* and/or *Salmonella agona*. Subspecies in O-serogroup $C_3$ can include *Salmonella Kentucky*. Subspecies in O-serogroup D can include *Salmonella enteritidis*. The antigen composition can be used alone or in combination with a Marek's Disease vaccine to reduce shedding of *E. coli* and/or *Salmonella* bacteria.

17 Claims, 1 Drawing Sheet

COMPOSITION AND METHOD FOR CONTROLLING INTESTINAL PATHOGENIC ORGANISMS

Figure 1:
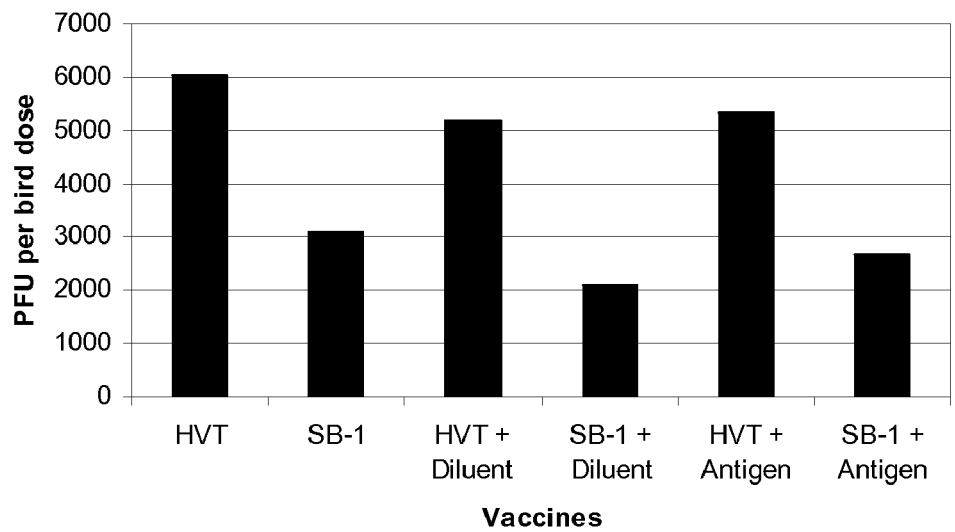

This application is a continuation-in-part application of U.S. patent application Ser. No. 11/737,483 filed on 19 Apr. 2007.

FIELD OF THE INVENTION

The invention pertains generally to composition for controlling intestinal pathogenic organisms in avian species and, more particularly, to a multivalent antigen for inducing immunity to specific bacterial diseases and/or to enhance immunity in an infected organism.

BACKGROUND OF THE INVENTION

Consumption of poultry products contaminated with *Salmonella* bacteria is a significant source of gastrointestinal infections in humans. For example, *Salmonella enteritidis*, especially phage type 4, has become more common in both poultry and humans since the early 1980's. The prevalence of *Salmonella typhimurium*, on the other hand, has remained relatively stable. However, the spread of the antibiotic-resistant strain DT104 in domestic flocks gives some reason for concern. Accordingly, the presence of *Salmonella* in commercial meat and food products is a major public health concern given that such infections can lead to serious illness or, in severe cases, death. Further, *Salmonella* infections in chickens, turkeys and ducks raise concerns for poultry producers due to increasing rates of morbidity and mortality as well as losses attributable culling and/or rejection of infected birds.

*Salmonella* infections can be spread via intraspecies or horizontal transmission, i.e., from animal to animal, and/or via interspecies or vertical transmission, i.e., from animal to humans. Generally, horizontal transmission of *Salmonella* bacteria is typically via exposure to environmental factors such as, for example, contaminated feces, bedding, nesting materials and/or other fomites. In contrast, vertical transmission of *Salmonella* bacteria is typically via oral exposure to the bacteria such by handling contaminated raw meats. Vertical transmission can also occur via shell contamination and/or internal transovarian contamination of the yolk of eggs produced by infected birds.

The basis for good control of *Salmonella* infections in farm environments, in particular, in poultry farms, is good farming and hygiene practices. Such practices include, for example, managing and preventing contamination of feeds, monitoring of animal health, cleaning and disinfection of coops and pens, and control of pest species such as, for examples, rodents. Testing and removal of infected or pathogen-positive animals from production and/or contact with uninfected animals are also vital to controlling horizontal and/or vertical transmission of such infections.

Poultry infected with *Salmonella* bacteria generally develop a strong immune response to the pathogen which is typically manifested by progressive reduction in excretion of the organism and reduced disease and excretion upon subsequent challenge. Accordingly, there is a need for an effective means for inducing an immune response to *Salmonella* bacteria in poultry which results in reduced disease and excretion or shedding of the bacteria while reducing productivity losses attributable to culling and/or rejection of infected birds.

Recently, vaccination of commercial poultry flocks to increase resistance against pathogenic exposure to *Salmonella* has become more prevalent particularly in view of increasing public awareness. However, such vaccination programs are generally difficult, time consuming and/or prohibitively expensive to administer on a commercial production scale. Accordingly, there is a need for an effective means for vaccinating domestic poultry and fowl against *Salmonella* infections.

Additionally, it is generally believed that vaccination is not a control option for serovars other than *Salmonella enteritidis* and *Salmonella typhimurium* which can be present on poultry farms. It is also generally believed that vaccination has limited effect on improving animal health and welfare and such vaccines are primarily used for public health reasons. Accordingly, there is a need for an antigen composition or vaccine effective to result in improved avian health and welfare such as can be manifested by increased weight gain and reduced mortality.

Further, some antigens may interfere with efficacy of other vaccines or medications administered simultaneously with and/or subsequent to vaccination. Additionally or alternatively, particular antigens may interfere with or affect the accuracy of traditional test or screening tools used to detect active or prior infection. Accordingly, there is a demand for a *Salmonella* antigen which can be administered to domestic poultry and fowl which does not reduce the effectiveness of other vaccines such as, for example, Marek's disease vaccines.

SUMMARY OF THE INVENTION

A general object of the invention is to provide a multivalent antigen for inducing an immune response and/or providing enhanced immunity to a pathogenic organism such as *Salmonella* spp.

A more specific object of the invention is to overcome one or more of the problems described above.

The general object of the invention can be obtained, at least in part, through a *Salmonella* multivalent antigen composition comprising or consisting of at least one *Salmonella enterica* subspecies in O-serogroup B, at least one *Salmonella enterica* subspecies in O-serogroup $C_3$, and at least one *Salmonella enterica* subspecies in O-serogroup D. The composition induces an immune response in an inoculated avian species to at least one intestinal pathogenic organism. The *Salmonella enterica* subspecies can include or consist of naturally-occurring wild strains from O-serogroups B, $C_3$ and/or D.

The prior art generally fails to provide a *Salmonella*-containing multivalent antigen composition which is as effective as desired in inducing an immune response to at least one intestinal pathogenic organism such as, for example, *Salmonella* spp. which is manifested by a reduced fecal count in an inoculated avian species. The prior art further generally fails to provide a multivalent antigen composition which can be easily and effectively administered in a commercial farm environment at a reduced cost. The prior art additionally fails to provide a multivalent antigen composition that can be utilized alone or in combination with other vaccine products without reducing the efficacy of either vaccine component and/or the ability to detect or diagnose particular diseases within inoculated birds.

The invention further comprehends a bacterin vaccine comprising or consisting of about 46% *Salmonella enterica* subspecies in O-serogroup B, about 31% *Salmonella enterica* subspecies in O-serogroup D, and about 23% *Salmonella enterica* subspecies in O-serogroup $C_3$. Subspecies in O-serogroup B can include or consist of *Salmonella typhimu-*

*rium, Salmonella agona* and/or combinations thereof. Subspecies in O-serogroup $C_3$ can include or consist of *Salmonella Kentucky*. Subspecies in O-serogroup D can include or consist of *Salmonella enteritidis* such as, for example, ATCC strain 13076.

The invention additionally comprehends an in ovo vaccine including a bacterin vaccine and a Marek's disease vaccine. The bacterin vaccine comprises or consists of ATCC strain 13076 of *Salmonella enteritidis*, ATCC strain 14028 of *Salmonella typhimurium, Salmonella agona*, and *Salmonella Kentucky*. The in ovo vaccine reduces a concentration of at least one pathogenic organism in a gastrointestinal tract of an inoculated avian species.

As used herein the term "bacterin" or "bacterin vaccine" refers to a vaccine composition generally comprised of dead or inactivated bacteria species.

As used herein the terms "about" and "substantially" when used in conjunction with a percentage or the term "equal" refer to a value falling within a range of ±1 percentage point. For example, a concentration of about 5% includes all concentrations falling within the range of 4% to 6%.

Other objects and advantages will be apparent to those skilled in the art from the following detailed description taken in conjunction with the examples and the appended claims.

BRIEF DESCRIPTION OF THE DRAWINGS

FIG. 1 is a chart showing the effect of an antigen composition of the invention on Marek's Disease vaccine titration in culture.

FIG. 2 is a chart showing the effect of an antigen composition of the invention on Marek's Disease vaccine re-isolation titers in vivo.

DETAILED DESCRIPTION

The invention provides a *Salmonella* multivalent antigen or antigen composition which stimulates an immune response in an inoculated avian species to at least one intestinal pathogenic organism. The *Salmonella* multivalent antigen composition can include or consist of *Salmonella enterica* subspecies from O-serogroups B, $C_3$ and D which in combination stimulate an immune response in an inoculated avian species to at least one intestinal pathogenic organism such as, for example, *Clostridium perfringens, Salmonella* species and/or *Escherichia coli.*

The *Salmonella* multivalent antigen composition can be employed alone and/or in combination with other bacterial strains, such as, for example, *E. coli, Pseudomonas aeruginosa*, and/or *Aerobacter aerogenes*, and/or other poultry vaccine compositions such as, for example, a Marek's disease vaccine. Further, the *Salmonella* multivalent antigen composition can be provided and/or utilized as a live or bacterin vaccine alone or in combination with other bacterial strains and/or poultry vaccine compositions.

Advantageously, the *Salmonella* multivalent antigen composition can be administered as an in ovo antigen vaccine. For example, the *Salmonella* multivalent antigen composition, such as in the form of a bacterin vaccine, can be utilized in a method for reducing the transmission of pathogenic gastrointestinal organisms that includes or consists of inoculating an avian species in ovo at about 18 days embryonic age with the bacterin vaccine.

Such a *Salmonella* multivalent antigen composition can include or consist of at least one *Salmonella enterica* subspecies in O-serogroup B, at least one *Salmonella enterica* subspecies in O-serogroup $C_3$ and at least on *Salmonella enterica* subspecies in O-serogroup D. Suitably, the *Salmonella enterica* subspecies include or consist of naturally-occurring wild strains from the O-serogroups B, $C_3$ and/or D.

It has been surprisingly discovered that a combination of *Salmonella enterica* subspecies from O-serogroups B, $C_3$ and D works synergistically to reduce not only the prevalence of *Salmonella* sp. but also other gastrointestinal pathogenic organisms in avian fecal matter. Without being bound thereby, it is believed that the combination of *Salmonella enterica* subspecies in O-serogroups B, $C_3$ and D work synergistically when administered in the form of a vaccine, and particularly in the form of an in ovo bacterin vaccine, to induce an immune response in inoculated avian species which reduces or eliminates colonization of gastrointestinal pathogens. Such immune response, induced preferably prior to hatch, has been found to reduce the prevalence of certain gastrointestinal pathogens such as, for example, *E. coli, Clostridium perfringens* and/or *Salmonella* spp., in avian fecal matter which in turn reduces the likelihood of vertical and/or horizontal transmission of such organisms to other species.

In accordance with certain embodiments, a *Salmonella* multivalent antigen composition can include or consist of about 46% *Salmonella enterica* subspecies in O-serogroup B, about 31% *Salmonella enterica* subspecies in O-serogroup D and about 23% *Salmonella enterica* subspecies in O-serogroup $C_3$.

*Salmonella enterica* subspecies in O-serogroup B can include or consist of *Salmonella typhimurium, Salmonella agona* and/or combinations thereof. In accordance with certain embodiments, the *Salmonella enterica* subspecies in O-serogroup B can include or consist of ATCC strain 14028 of *Salmonella typhimurium. Salmonella enterica* subspecies in O-serogroup $C_3$ can include or consist of *Salmonella Kentucky. Salmonella enterica* subspecies in O-serogroup D can include or consist of *Salmonella enteritidis* such as, for example, ATCC Strain 13076 of *Salmonella enteritidis.*

In accordance with certain embodiments, the *Salmonella* multivalent antigen composition can be included in an in ovo bacterin vaccine including or consisting of: a bacterin vaccine including or consisting of ATCC stain 13076 of *Salmonella enteritidis*, ATCC 14028 of *Salmonella typhimurium, Salmonella agona* and *Salmonella Kentucky*; and a Marek's disease vaccine such as, for example, an HVT vaccine, a SB-1 vaccine and/or a combination thereof. The in ovo bacterin vaccine reduces a concentration of at least one pathogenic organism in a gastrointestinal tract of an inoculated avian species such as, for example, domestic fowl selected from the group including but not limited to chickens, ducks, geese and/or turkeys. Such in ovo bacterin vaccine can be administered to the avian species at about 18 day's embryonic age.

In accordance with another aspect, the *Salmonella* multivalent antigen composition forms an integral part of a multivalent antigen composition that includes or consists of other and/or additional bacterial strains and/or poultry vaccine compositions. For example, the multivalent antigen composition can include seven field strains of *E. coli, Pseudomonas aeruginosa, Aerobacter aerogenes, Salmonella enteritidis, Salmonella typhimurium, Salmonella agona* and *Salmonella Kentucky.*

In accordance with certain embodiments, the multivalent antigen or antigen composition stimulates an immune response to an intestinal pathogenic organism selected from *Clostridium perfringens, Salmonella* spp., *E. coli* or a combination thereof Such immune response can be manifested as a reduction in fecal bacterial counts for a particular pathogen such as, for example, reduction in *Salmonella* spp. fecal bacteria counts and/or *E. coli* fecal bacterial counts. Such immune response can additionally or alternatively be manifested as a reduction in lesion formation upon exposure to *Clostridium perfringens*.

Various strains of *E. coli* bacteria can be included in the antigen composition. Suitably, such strains of *E. coli* bacteria can be selected from ATCC strain 25922, a University of Delaware field isolate, one or more Delmarva field isolates or a combination thereof. In accordance with one embodiment, the antigen composition includes seven field strains of *E. coli* bacteria including ATCC strain 25922, a University of Delaware field isolate and five Delmarva field isolates.

In accordance with certain embodiments, the antigen composition includes about 67% of seven strains of *E. coli* bacteria. Suitably, each strain of *E. coli* bacteria is present in an approximately equal amount.

Various strains of *Pseudomonas aeruginosa* are suitable for use in the antigen composition. In accordance with one embodiment, the antigen composition can include ATCC strain 27653 of *Pseudomonas aeruginosa*. Suitably, the antigen composition can include about 10% *Pseudomonas aeruginosa.*

The antigen composition further includes *Aerobacter aerogenes* such as in a concentration of about 10%. In accordance with certain aspects of the invention, the antigen composition is or should be free or devoid of *Enterobacter aerogenes* and/or *Klebsiella pneumoniae.*

The antigen composition also includes at least four strains of *Salmonella* species. In particular, the antigen composition includes *Salmonella enteritidis, Salmonella typhimurium, Salmonella agona* and *Salmonella Kentucky*. In accordance with certain embodiments, the antigen composition can include ATCC strain 13076 of *Salmonella enteritidis* and/or ATCC strain 14028 of *Salmonella typhimurium.*

Suitably, the antigen composition, in accordance with one embodiment, can include about 4% *Salmonella enteritidis*, about 3% *Salmonella typhimurium*, about 3% *Salmonella agona* and about 3% *Salmonella Kentucky.*

Suitably, the multivalent antigen or antigen composition can be utilized as or in an in ovo vaccine for inoculating avian species or domestic fowl. For example, about 0.005 ml to about 0.05 ml of the multivalent antigen or antigen composition can be used to inoculate an embryonated egg. In accordance with certain embodiments, the multivalent antigen or antigen composition can be given in a dose of about 0.0063 ml to about 0.0375 ml per embryonated egg.

The multivalent antigen or antigen composition is suitable for use alone as a bacterin vaccine or in combination with one or more other vaccine preparations. For example, the antigen composition can be administered sequentially with or simultaneously with another vaccine preparation such as, for example, a Marek's Disease vaccine.

In accordance with one embodiment, the antigen composition can be mixed or combined with a Marek's Disease vaccine. Such combined or mixed vaccine comprises a bacterin vaccine including seven strains of *E. coli, Pseudomonas aeruginosa, Aerobacter aerogenes, Salmonella enteritidis, Salmonella typhimurium, Salmonella agona* and *Salmonella Kentucky* and a Marek's Disease vaccine. The Marek's Disease vaccine can include an HVT vaccine, a SB-1 vaccine or a bivalent vaccine including a mixture or combination of HVT and SB-1 strains. Advantageously, the bacterin and Marek's Disease vaccine may be combined in any suitable ratio. For example, the combined vaccine may have a bacterin vaccine to Marek's Disease vaccine ratio in the range of about 1:15 to 15:1. In accordance with certain embodiments, the bacterin vaccine and the Marek's Disease vaccine can be combined in a 1:1 ratio.

The combined bacterin-Marek's Disease vaccine reduces a concentration of at least one pathogenic organism in a gastrointestinal tract of an inoculated avian species. Such pathogenic organism can include *E. coli, Salmonella* spp. or a combination thereof.

Suitably, the combined bacterin-Marek's Disease vaccine can be an in ovo vaccine suitable for inoculating an avian species or domestic fowl such as, for example, chickens, ducks, geese and/or turkeys. For example, the combined bacterin-Marek's Disease vaccine can be administered in ovo in a dose of about 0.005 ml to about 0.1 ml combined vaccine per embryonated egg. In accordance with certain embodiments, a dose of the combined bacterin-Marek's Disease vaccine can include about 0.0063 ml to about 0.0375 ml bacterin vaccine.

A method for reducing transmission of pathogenic gastrointestinal organisms includes inoculating an avian species in ovo at about 18 days embryonic age with the above-described antigen composition alone such as, for example, as a bacterin vaccine or in combination with another vaccine preparation such as, for example, a Marek's Disease vaccine.

EXAMPLES

Antigen Composition

An antigen composition was produced using various strains of bacteria, shown in TABLE 1, below, commonly found in poultry and/or humans. Each bacteria isolate was initially individually grown in 1000 ml of Nutrient Broth (Sigma N7519) at 35±1° C. for 24±2 hours. After the incubation period, each broth was centrifuged for approximately 10 minutes at 5000 rpm in individual centrifuge sectors to separate the cells from the broth. The supernatant was then aseptically removed from each centrifuge vessel. The remaining cultures from each tube were then re-suspended in Butterfield's Phosphate diluent and tested to determine purity. The purified cultures collectively formed a Master Seed.

The above steps were repeated until the quantity of Master Seed required to produce mass quantities of Working Seed stock was achieved. Following determination of purity and specie, all Working Seed stock batches were mixed, separated into batch fermentation vessels and grown at 35±1° C. for 24±2 hour periods. At the completion of each batch, the entire batch was carefully mixed and a sample of each culture was then plated onto Nutrient Agar. Colonies were counted after a further incubation period of 24±2 hours at 35±1° C. using 10-fold dilutions up to $10^{10}$ dilution rate. Plates with CFUs between 30 and 300 were counted.

TABLE 1

| Bacterial component | CFU Counts |
|---|---|
| *E. coli* Isolate #1 | $1.36 \times 10^{10}$ |
| *E. coli* Isolate #2 | $2.03 \times 10^{10}$ |
| *E. coli* Isolate #3 | $6.80 \times 10^{9}$ |
| *E. coli* Isolate #4 | $2.92 \times 10^{10}$ |
| *E. coli* Isolate #5 | $1.28 \times 10^{10}$ |
| *E. coli* Isolate #6 | $2.13 \times 10^{10}$ |
| *E. coli* Isolate #7 | $5.30 \times 10^{10}$ |
| *Pseudomonas aeruginosa* | $2.14 \times 10^{9}$ |
| *Aerobacter aerogenes* | $9.40 \times 10^{8}$ |
| *Salmonella enteritidis* | $1.86 \times 10^{9}$ |
| *Salmonella typhimurium* | $2.38 \times 10^{9}$ |
| *Salmonella agona* | $4.10 \times 10^{9}$ |
| *Salmonella Kentucky* | $6.50 \times 10^{9}$ |

The final counts were used to dilute and mix the individual cultures into the final antigen composition or bacterin vaccine, as shown in TABLE 2, below. The bacteria were then killed by autoclaving at 121° C. for 15±2 minutes. This procedure was then repeated to ensure total bacteria kill.

TABLE 2

| Bacterial Component | Concentration |
| --- | --- |
| E. coli (7 field strains) | 67% (each strain in ≈ equal amounts) |
| Pseudomonas Aeruginosa | 10% |
| Aerobacter aerogenes | 10% |
| Salmonella enteritidis | 4% |
| Salmonella typhimurium | 3% |
| Salmonella agona | 3% |
| Salmonella Kentucky | 3% |

Effect on Lesion Formation Due to *Clostridium Perfringens* Exposure

Fourteen treatment groups of Ross (Male)×Cobb (Female) broilers were in ovo inoculated with either a saline control or the antigen composition described in TABLE 2 at an embryonic age of 18 days. The fourteen treatment groups include seven (7) control groups each including 20 male and 20 female chicks and seven (7) vaccine groups each including 20 male and 20 female chicks.

All birds were inoculated with *Clostridium perfringens* ($10^4$ per bird) on post-hatch Day 8 to induce necrotic enteritis. Four male and four female birds from each control group and each vaccine group were humanely euthanized on Days 21 and 49, necropsied and the intestinal tracts visually inspected for signs of necrotic enteritis and/or coccidiosis. The intestinal lesion scores including both coccidiosis signs and necrotic enteritis signs were recorded. Lesions were scored on a scale of 0 to 4 as follows:

0=No lesions found;
1=Slight redness with no cell sloughing (mucus);
2=Moderate redness and/or slight cell sloughing;
3=Severe redness and/or severe cell sloughing; and
4=Actual bleeding observed.

The lesion score data, as summarized in TABLE 3, below, indicate that birds inoculated with the above-described antigen composition or bacterin vaccine had a statistically lower rate of development of intestinal lesions between Days 8 and 21. Lesion scores recorded on Day 49 for both the control and vaccinated populations were not significantly different. Accordingly, it is believed that inoculation with the antigen composition of the invention induces an immune response to the intestinal pathogen *Clostridium perfringens* thereby reducing the incidence, duration and/or severity of necrotic enteritis in avian populations.

Effect on Preharvest Intestinal Crop Bacteria.

All of the birds from the fourteen treatment groups described above were additionally inoculated with *Escherichia coli* ($10^6$ per bird) and *Salmonella* spp. ($10^4$ per bird) administered via oral gavage on post-hatch Day 15. Eight birds (4 males and 4 females) from each control and each vaccine group were humanely euthanized and necropsied on post-hatch Days 21 and 49. Crop content bacteria from each bird were plated on an appropriate agar and fecal *E. coli* and *Salmonella* spp. bacteria counts were recorded.

The fecal bacteria data, summarized in TABLE 3, below, indicate that birds inoculated with above-described antigen composition or bacterin vaccine had a statistically lower concentration of both *E. coli* and *Salmonella* bacteria present in the crop contents. Accordingly, it is believed that inoculation with the antigen composition of the invention induces or stimulates an immune response to *E. coli* and *Salmonella* resulting in reduced fecal bacteria content as well as reduced shedding of bacteria.

Additionally, it was determined, as summarized in TABLE 3, below, that birds inoculated with the above-described antigen composition exhibited an increase in average weight gain over the duration of the 49 day study.

TABLE 3

| | Day 21 | | Day 49 | |
| --- | --- | --- | --- | --- |
| Criterion | Control | Vaccine | Control | Vaccine |
| Average Lesion Score | 1.018 | 0.250 | 0.179 | 0.107 |
| Std Dev. | 0.29 | 0.09 | 0.15 | 0.10 |
| C.V. | 28.93 | 37.80 | 82.46 | 97.18 |
| Fecal *E. coli* count (per ml) | 2085.0 | 786.2 | 1479.9 | 532.1 |
| Std Dev. | 158.80 | 138.90 | 161.02 | 67.59 |
| C.V. | 7.62 | 17.67 | 10.88 | 12.70 |
| Fecal *Salmonella* spp. count (per ml) | 160.0 | 122.4 | 129.7 | 94.7 |
| Std Dev. | 16.85 | 11.10 | 12.86 | 9.98 |
| C.V. | 10.53 | 9.07 | 9.92 | 10.54 |
| Average Weight Gain (g) | 547.648 | 580.171 | 2146.721 | 2225.416 |
| Std Dev. | 7.13 | 7.97 | 58.50 | 59.18 |
| C.V. | 1.30 | 1.37 | 2.72 | 2.66 |

Effect on Marek's Disease Vaccine

A study was conducted to determine if the above-described antigen composition or bacterin vaccine if administered in combination with commercially available Marek's Disease vaccine negatively impacted the replication of the vaccine viruses in cell culture or in vivo. Such a negative impact, as determined by decreases in the ability to re-isolate vaccine viruses at one week post-hatch, would suggest that the antigen composition may decrease Marek's Disease vaccine efficacy.

Effect on Marek's Disease Vaccine in Culture.

To assess the effect of the above-described antigen composition on Marek's Disease vaccine preparations, the antigen composition and its diluent were obtained at 4× concentration. These were added to 4× stocks of HVT and SB-1 to generate 2× stocks of HVT and SB-1. Upon mixing of equal amounts, this yielded 1× bivalent vaccines containing either 1× diluent or 1× antigen composition.

The vaccine stocks were titrated independently from the 4× stocks and also titrated from each of the 1× final stocks. This was to determine the effect of the antigen composition on HVT and SB-1 replication, in culture and to determine if the antigen composition would interfere with titration of commercial vaccine. In each case, a commercial diluent was used for diluting the vaccines. Vaccine, viruses and diluent were obtained from commercial sources.

As indicated by the titration data, summarized in TABLE 4, below, and shown in FIG. 1, the antigen composition did not negatively affect Marek's Disease replication in cell culture. Titration of the vaccine stocks after either diluent or antigen composition addition showed essentially identical titers.

TABLE 4

| Vaccine | PFU/Vial | Dose | Dilution | Mean Plaque # | Bird Dose (PFU) | Std Dev. |
|---|---|---|---|---|---|---|
| HVT | $1.59 \times 10^7$ | 4X | 1:50 | 120.8 (±8.5) | 6040 | 1028 |
| SB-1 | $4.2 \times 10^5$ | 4X | 1:50 | 123 (±14) | 3075 | 742 |
| HVT + diluent | | 1X | 1:100 | 51.75 (±7.5) | 5175 | 750 |
| SB-1 + diluent | | 1X | 1:100 | 20.75 (±6.4) | 2075 | 640 |
| HVT + antigen | | 1X | 1:100 | 53.3 (±3.9) | 5325 | 386 |
| SB-1 + antigen | | 1X | 1:100 | 26.5 (±3.9) | 2650 | 387 |

Effect on Marek's Disease Vaccine In Vivo.

Eggs from a commercial broiler chicken strain, Ross X Cobb breed, were inoculated at 18 days embryonic age with either a bivalent HVT/SB-1 Marek's Disease vaccine (5000 PFU/bird HVT+2500 PFU/bird SB-1) mixed with a control diluent (vaccine+diluent) or a vaccine including the bivalent Marek's Disease vaccine mixed with the above-described antigen composition (vaccine+antigen). Post-hatch, an equal number of male and female chicks were randomly placed in grow out pens and grown under practical commercial conditions.

At one week post-hatch chickens were bled via cardiac puncture, euthanized and the spleens were pooled into groups. The vaccine+diluent and vaccine+antigen groups were each comprised of four (4) pools of three (3) birds.

Blood and spleens were pooled and PBMC were purified from the whole blood by histopaque centrifugation. Spleen cells were washed, counted and plated at $2\times10$ cells in triplicate dishes for each pool. PBMC were not co-cultivated with CEF monolayers, as HVT and SB-1 infection is characteristically low at this time. At six (6) days post-plating, the dishes were examined and plaques for HVT and SB-1 were counted.

Figure 2:
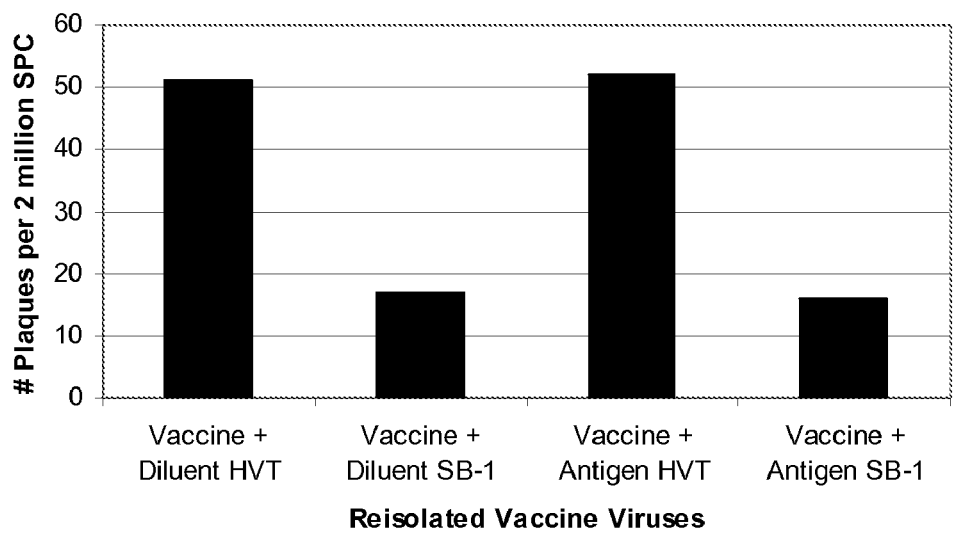

The above procedure was repeated three times over the course of four (4) weeks, i.e., a total of 16 pools of birds from the vaccine+diluent and a total of 16 pools of birds from the vaccine+antigen groups were inoculated and evaluated. The data obtained from the re-isolation counts were subjected to Chi-square and Students t-test analysis, the results of which are summarized in TABLE 5, below, and shown in FIG. 2.

TABLE 5

| Vaccine + Diluent | | | Vaccine + Antigen | | |
|---|---|---|---|---|---|
| Group # | Strain | Count | Group # | Strain | Count |
| 1A | HVT | 48 ± 1 | 1B | HVT | 47 ± 13 |
| | SB-1 | 21 ± 3 | | SB-1 | 13 ± 1 |
| 2A | HVT | 58 ± 14 | 2B | HVT | 56 ± 22 |
| | SB-1 | 16 ± 3 | | SB-1 | 19 ± 2 |
| 3A | HVT | 67 ± 16 | 3B | HVT | 37 ± 2 |
| | SB-1 | 17 ± 4 | | SB-1 | 15 ± 2 |
| 4A | HVT | 42 ± 1 | 4B | HVT | 69 ± 8 |
| | SB-1 | 25 ± 5 | | SB-1 | 20 ± 1 |
| HVT Overall Average | | 54 | HVT Overall Average | | 52 |
| SB-1 Overall Average | | 20 | HVT Overall Average | | 17 |

The results in TABLE 5 indicate that comparable counts of HVT and SB-1 plagues were obtained from the two treatment groups and, thus, overall no significant differences were found for either the HVT or the SB-1 data.

In Week 4 of the study, a statistically significant difference was found in the HVT counts between the vaccine+diluent and the vaccine+antigen groups. The antigen was found to increase the titers of HVT re-isolated from inoculated chickens at one-week post-hatch. This is believed to indicate an advantage conferred on the replication of HVT. Conversely, a small but statistically significant difference was found between SB-1 re-isolated from the inoculated chickens.

Overall, the bacterin vaccine or antigen composition did not negatively affect Marek's Disease replication in vivo. Thus, it is unlikely that the antigen composition would decrease the efficacy of Marek's Disease vaccines if employed in an in ovo vaccination program. Moreover, the addition of the antigen composition should not negatively affect the ability to titer vaccines.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

What is claimed is:

1. An antigen composition, comprising:

at least one *Salmonella enterica* subspecies in O-serogroup B;

at least one *Salmonella enterica* subspecies in O-serogroup $C_3$; and at least one *Salmonella enterica* subspecies in O-serogroup D;

the antigen composition stimulating an immune response in an inoculated avian species to at least one intestinal pathogenic organism, wherein the antigen is an in ovo vaccine and wherein the *Salmonella enterica* subspecies *comprise* inactivated naturally-occurring wild strains from the O-serogroups B, $C_3$, and D.

2. The antigen composition of claim 1, wherein the intestinal pathogenic organism comprises *Clostridium perfringens.*

3. The antigen composition of claim 1, wherein the intestinal pathogenic organism comprises *Salmonella* species.

4. The antigen composition of claim 1, wherein the intestinal pathogenic organism comprises *Escherichia coli.*

5. The antigen composition of claim 1, wherein the at least one *Salmonella enterica* subspecies in O-serogroup B is selected from *Salmonella typhimurium, Salmonella* agona and combinations thereof.

6. The antigen composition of claim 1, wherein the at least one *Salmonella enterica* subspecies in O-serogroup $C_3$ comprises *Salmonella Kentucky.*

7. The antigen composition of claim 1, wherein the at least one *Salmonella enterica* subspecies in O-serogroup D comprises *Salmonella enteritidis.*

8. A bacterin vaccine, comprising:

about 46% *Salmonella enterica* subspecies in O-serogroup B;

about 31% *Salmonella enterica* subspecies in O-serogroup D; and about 23% *Salmonella enterica* subspecies in O-serogroup $C_3$, wherein the bacterin vaccine is an in ovo vaccine comprising naturally-occurring wild *Salmonella enterica* subspecies from the B, $C_3$, and D O-serogroups.

9. The bacterin vaccine of claim 8, wherein the *Salmonella enterica* subspecies in O-serogroup B comprise *Salmonella Typhimurium, Salmonella agona*, or a combination thereof.

10. The bacterin vaccine of claim 8, wherein the *Salmonella enterica* subspecies in O-serogroup D comprises *Salmonella enteritidis*.

11. The bacterin vaccine of claim 10, wherein the *Salmonella enterica* subspecies in O-serogroup $C_3$ comprises *Salmonella Kentucky*.

12. A method for reducing transmission of pathogenic gastrointestinal organisms, comprising:
    inoculating an avian species in ovo at about 18 days embryonic age with the vaccine according to claim 8.

13. An in ovo bacterin vaccine, comprising:
    a bacterin vaccine including naturally-occurring wild strains of:
    *Salmonella enteritidis,*
    *Salmonella typhimurium,*
    *Salmonella agona,* and
    *Salmonella Kentucky*; and
    a vaccine effective against Marek's disease,
    the in ovo bacterin vaccine reducing a concentration of at least one pathogenic organism in a gastrointestinal tract of an inoculated avian species.

14. The in ovo vaccine of claim 13, wherein the Marek's disease vaccine is selected from the group consisting of HVT vaccines, SB-1 vaccines, and combinations thereof.

15. The in ovo vaccine of claim 13, wherein the pathogenic organism is selected from the group consisting of *E. coli* spp., *Salmonella* spp., or a combination thereof.

16. The in ovo vaccine of claim 13, wherein the avian species is a domestic fowl selected from the group consisting of chickens, ducks, geese and turkeys.

17. A method for reducing transmission of pathogenic gastrointestinal organisms, comprising:
    inoculating an avian species in ovo at about 18 days embryonic age with the vaccine according to claim 13.

* * * * *

UNITED STATES PATENT AND TRADEMARK OFFICE
CERTIFICATE OF CORRECTION

| | | |
|---|---|---|
| PATENT NO. | : 7,935,355 B2 | Page 1 of 1 |
| APPLICATION NO. | : 12/025568 | |
| DATED | : May 3, 2011 | |
| INVENTOR(S) | : Konky Sotomayor | |

It is certified that error appears in the above-identified patent and that said Letters Patent is hereby corrected as shown below:

In Column 11, line 10, change "10" to --8--.

Signed and Sealed this
Second Day of August, 2011

David J. Kappos
*Director of the United States Patent and Trademark Office*